United States Patent
Pflueger et al.

(10) Patent No.: US 7,181,289 B2
(45) Date of Patent: Feb. 20, 2007

(54) EPIDURAL NERVE ROOT ACCESS CATHETER AND TREATMENT METHODS

(76) Inventors: D. Russell Pflueger, 160 Monarch Bay Dr., Monarch Beach, CA (US) 92629; Robert E. Wright, 19 Covington Ct., Englewood, CO (US) 80110

( * ) Notice: Subject to any disclaimer, the term of this patent is extended or adjusted under 35 U.S.C. 154(b) by 425 days.

(21) Appl. No.: 10/692,021

(22) Filed: Oct. 23, 2003

(65) Prior Publication Data

US 2005/0060006 A1 Mar. 17, 2005

Related U.S. Application Data

(63) Continuation-in-part of application No. 09/813,067, filed on Mar. 20, 2001, now abandoned.

(60) Provisional application No. 60/190,760, filed on Mar. 20, 2000.

(51) Int. Cl.
*A61N 1/00* (2006.01)
*A61M 31/00* (2006.01)

(52) U.S. Cl. .................. 607/117; 607/46; 600/500; 606/129

(58) Field of Classification Search ................ 607/117, 607/46; 604/500; 128/898; 600/585, 101; 606/129
See application file for complete search history.

(56) References Cited

U.S. PATENT DOCUMENTS

| | | |
|---|---|---|
| 4,817,613 A | 4/1989 | Jaraczewski et al. |
| 5,562,722 A | 10/1996 | Racz et al. |
| 5,591,132 A | 1/1997 | Carrie |
| 5,658,263 A | 8/1997 | Dang et al. |
| 5,713,858 A | 2/1998 | Heruth et al. |
| 5,769,830 A | 6/1998 | Parker |
| 5,785,705 A | 7/1998 | Baker |
| 5,810,788 A | 9/1998 | Racz |
| 5,817,074 A | 10/1998 | Racz |
| 5,857,996 A | 1/1999 | Snoke |
| 5,860,963 A | 1/1999 | Azam et al. |
| 5,885,247 A | 3/1999 | Slagboom |
| 5,938,690 A | 8/1999 | Law et al. |
| 5,957,911 A | 9/1999 | Nesto |
| 5,980,504 A | 11/1999 | Sharkey et al. |
| 6,002,964 A | 12/1999 | Feler et al. |
| 6,007,570 A | 12/1999 | Sharkey et al. |
| 6,010,493 A | 1/2000 | Snoke |

OTHER PUBLICATIONS

Santiago et al., Morphometry of the lower lumbar vertebrae in patients with and without low back pain, Springer-Verlag, 2001.

Baz et al, The role of computerized tomography to the establishment of the morphological aspects of the lumbar vertebral canal, ERC 91 Presentation11-085.

Karantanas et al., Normal dimensions of the lumbar spinal canal: A computed tomography study, ERC 97 Presentation129.

*Primary Examiner*—Mark Bockelman
(74) *Attorney, Agent, or Firm*—Stout, Uxa, Buyan & Mullins LLP; Frank J. Uxa

(57) ABSTRACT

Apparatus and methods for accessing and/or treating spinal cord nerve roots.

13 Claims, 3 Drawing Sheets

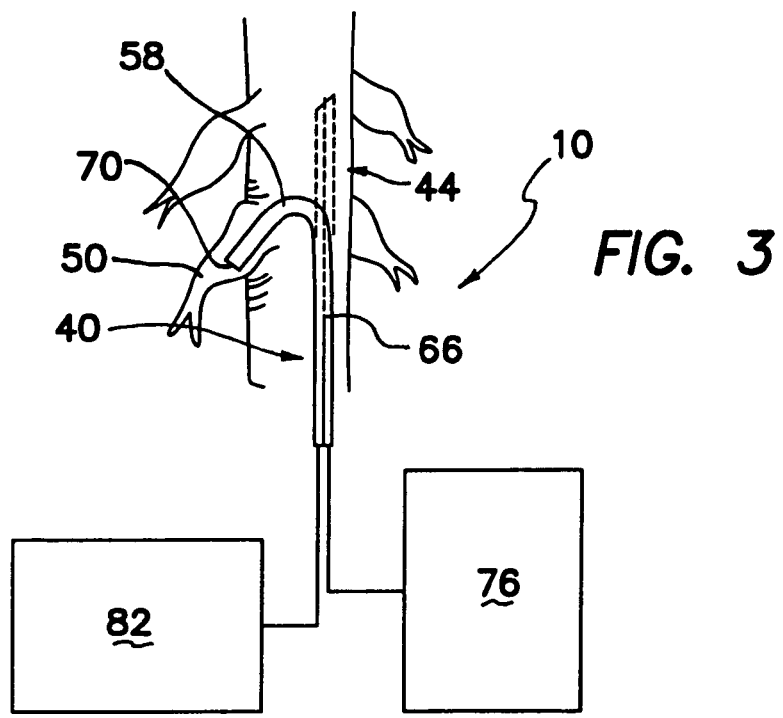
FIG. 3
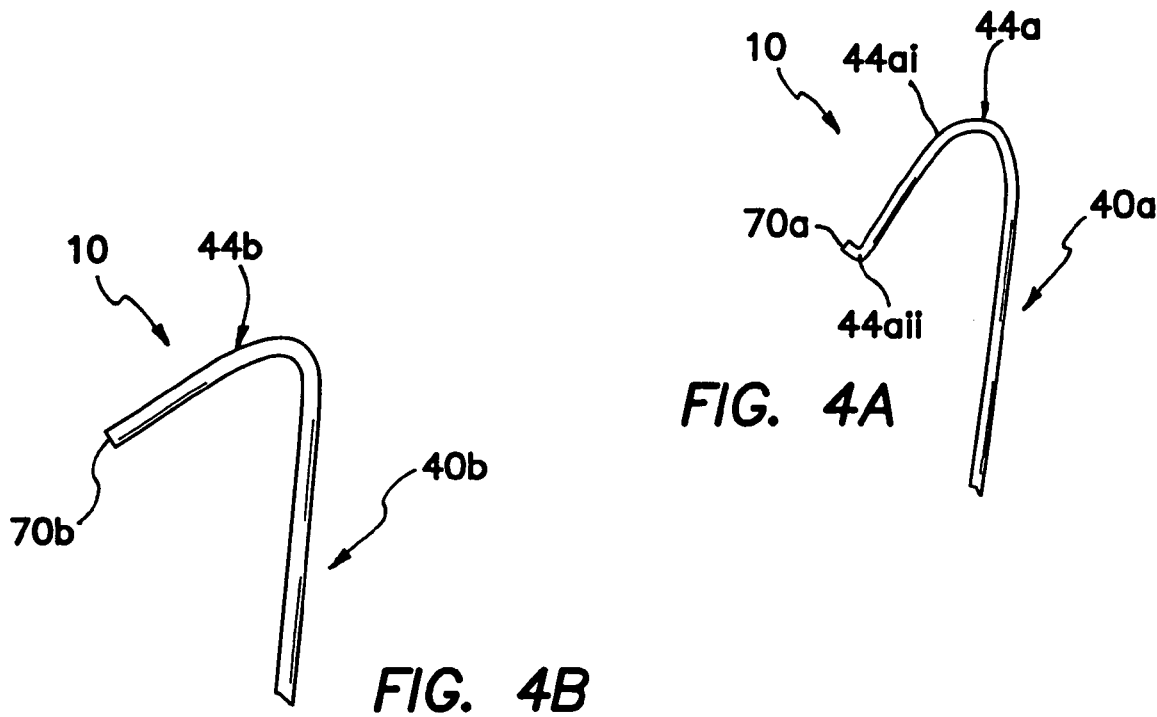
FIG. 4A
FIG. 4B

EPIDURAL NERVE ROOT ACCESS CATHETER AND TREATMENT METHODS

RELATED APPLICATION

This application is a continuation-in-part of U.S. patent application Ser. No. 09/813,067, filed on Mar. 20, 2001 now abandoned, which claims the benefit of U.S. provisional application Ser. No. 60/190,760 filed Mar. 20, 2000, the disclosure of each of which is incorporated in its entirety herein by this specific reference.

FIELD OF THE INVENTION

The present invention relates generally to apparatus comprising catheters and to methods, and more particularly, to such apparatus and methods for accessing and/or treating a spinal column, or an area in proximity to a spinal column, for example, for accessing and/or treating spinal cord nerve roots.

BACKGROUND OF THE INVENTION

The medical industry is constantly evolving through the adaptation of improved pharmaceutical, biotechnology, and medical device products and procedures. Techniques and technologies are constantly being developed to treat internal areas of the body through less invasive means. Catheters, fiberoptic scopes, and miniature devices are being designed to access, image, and treat desired areas.

Recently, devices have been developed to explore and therapeutically impact areas inside the spinal canal. These devices are primarily designed to reduce the amount of pain that chronic pain patients are experiencing due to abnormal conditions existing in and around the spinal cord. Devices currently used to treat these areas include spinal injections of anesthetics and anti-inflammatories, RF and cryo neuroablation, epiduroscopes, spinal stimulation, implantable pumps, and the like.

Snoke, U.S. Pat. No. 5,857,996, issued on Jan. 12, 1999, which is incorporated herein in its entirety by this specific reference, discloses a method of epidural surgery that involves distending a portion of an epidural space with a fluid supplied from a catheter in order to facilitate observation of structures within the epidural space. Snoke discloses that the catheter is initially inserted into the sacral foramen and advanced to a desired spinal level. The catheter is then used for supplying a fluid to infuse and distend the epidural space. According to Snoke, a fiberoptic scope is then inserted through the catheter to the distended portion of the epidural space to allow observation thereof.

There continues to be a need for apparatus and methods for imaging and/or treating structures in or near the spinal column.

SUMMARY OF THE INVENTION

New apparatus and methods for treating and/or imaging areas inside the spinal canal have been discovered.

In one broad aspect of the invention, apparatus for treating a human or animal patient are provided. The apparatus generally comprises a catheter device sized to be placed in an epidural space of a spinal canal of a patient. The catheter device includes a distal region having a pre-formed configuration, preferably a curved configuration defined by one or more curves, for example, arcuate curves.

Advantageously, the pre-formed configuration of the distal region has a shape and degree of curve that is selected to facilitate access to a target nerve root within the spinal canal of the patient. For example, the distal region of the catheter device may include at least one region generally not aligned along a longitudinal axis of the catheter device, such region being defined by a bend, arc, curve, or other contoured region (hereinafter generally referred to as a "curve"). The distal region generally curves in a retrograde direction and terminates in a distal tip generally positioned spaced apart from the longitudinal axis of the catheter.

For example, the distal region may comprise a curve defining an angle of at least about 90 degrees up to about 160 degrees with respect to the longitudinal axis. In one embodiment, the angle is greater than about 90 degrees.

In some embodiments of the invention, the distal region may additionally include one or more secondary curves for providing greater precision and further facilitating access to a specific target site within the epidural space. Such secondary curve or curves are often located distally of the primary curve.

Advantageously, the catheter device is structured to enable the pre-formed distal region to be substantially straightened in order to facilitate insertion and advancement of the device along the spinal canal. The catheter device may, and preferably does, include a lumen extending from a proximal region to the distal region of the catheter device wherein the lumen is sized to accommodate a guidewire for straightening the pre-formed configuration.

Preferably, the pre-formed configuration has a span, for example, a length or diameter, sufficient to extend a width of the epidural space at the site of interest.

The pre-formed configuration of the distal region of the catheter preferably includes a diameter approximately equal to or greater than a posterior vertebral canal space of the human or animal.

Preferably, the pre-formed configuration is structured so as to allow a portion of the distal region catheter device to engage a pedicle above (or closer to the top of the head of the patient relative to) the targeted nerve root and/or to be supported by, or buttressed against an opposite wall of the epidural space, in order to secure the distal tip of the catheter device in proximity to the nerve root.

The distal region of the catheter device preferably has a configuration, size and shape such that when the distal region is in the pre-formed configuration and the catheter device is buttressed against a wall of the epidural space, the distal portion sweeps across, or spans, the epidural space to an opposing side of the epidural space and the distal tip of the catheter device is about in proximity to, for example, in contact with, the target nerve root.

The various spinal nerves of a human or animal patient are disposed at somewhat predictable, measurable positions and angles with respect to the longitudinal axis of the spinal cord from which they radiate.

Advantageously, the pre-formed configuration is selected based upon a particular nerve or other targeted site within the spinal canal. The pre-formed configuration is preferably structured to enable selective access to a particular nerve root of interest. In one embodiment, a set of differently sized and/or configured catheter devices are provided in accordance with the present invention to provide for imaging/treatment of different sized patients and/or at different locations in the spinal canal (at different nerve roots).

When configured for access in the spinal nerves in the lumbar and thoracic regions of the spine, the catheter device advantageously includes a distal region having a single primary curve of at least about 90 degrees or more and a curve span or length of about 1.0 centimeter to about 2.0 centimeters.

Advantageously, the apparatus is structured to enable access to and/or treatment of the nerve root or structures and tissues adjacent the nerve, for example, delivery of a medicament, removal of tissue in or around the nerve root, delivery of a radio-opaque material, electrical stimulation and/or ablation of tissue at the targeted site.

For example, the catheter device may be structured to deliver electrical stimulation to the nerve root in order to treat pain.

In a further broad aspect of the present invention, methods of imaging and/or treating a spinal nerve root are provided. Such methods may comprise using the apparatus of the present invention described elsewhere herein.

The methods of the present inventions generally comprise the steps of providing a catheter device sized to be placed in an epidural space of a spinal canal of a patient. The catheter device has a distal region with a pre-formed configuration, for example a non-linear configuration, such as an arcuate, angular or bended configuration. This pre-formed distal region of the catheter device is provided in a substantially straightened configuration, for example by providing a guidewire within a lumen of the catheter device.

The method further comprises the steps of introducing the distal region of the catheter device into a sacral hiatus of a patient, and advancing, while in a substantially straightened configuration, the distal region of the catheter device anterogradely, or cephalically, through the epidural canal from the sacral hiatus to a site adjacent, and sometimes slightly anterograde, of a targeted nerve root.

The method further comprises the step of positioning the distal tip of the catheter device in proximity to the targeted nerve root in order to contact or provide direct access to the targeted nerve root. The step of positioning is accomplished by causing the distal region of the catheter device to assume or resume its pre-formed configuration, thereby allowing the distal region to move in a somewhat retrograde direction, sweeping across the epidural space, and contacting or otherwise providing access to the targeted nerve root.

The step of positioning may include withdrawing the guidewire from the catheter device lumen in order to cause the distal region of the catheter device to resume its preformed configuration while in the desired site within the epidural space.

The method may include one or more of the steps of delivering a medicament, delivering radio-opaque dye, delivering electrical stimulation and delivering ablation into the nerve root and/or structures and/or tissues in proximity thereto, through the distal tip of the catheter device.

Each and every feature described herein, and each and every combination of two or more of such features, is included within the scope of the present invention provided that the features included in such a combination are not mutually inconsistent.

These and other aspects and advantages of the present invention are apparent in the following detailed description and claims, particularly when considered in conjunction with the accompanying drawings in which like parts bear like reference numerals.

BRIEF DESCRIPTION OF THE DRAWINGS

FIG. 3 is a simplified diagram of a distal region of the catheter apparatus as it is being used to treat or image a nerve root.

FIG. 4a–4b show alternative pre-formed distal regions of other embodiments of the present invention, having alternative pre-formed configurations for targeting different nerve roots.

DETAILED DESCRIPTION OF THE INVENTION

Figure 1:
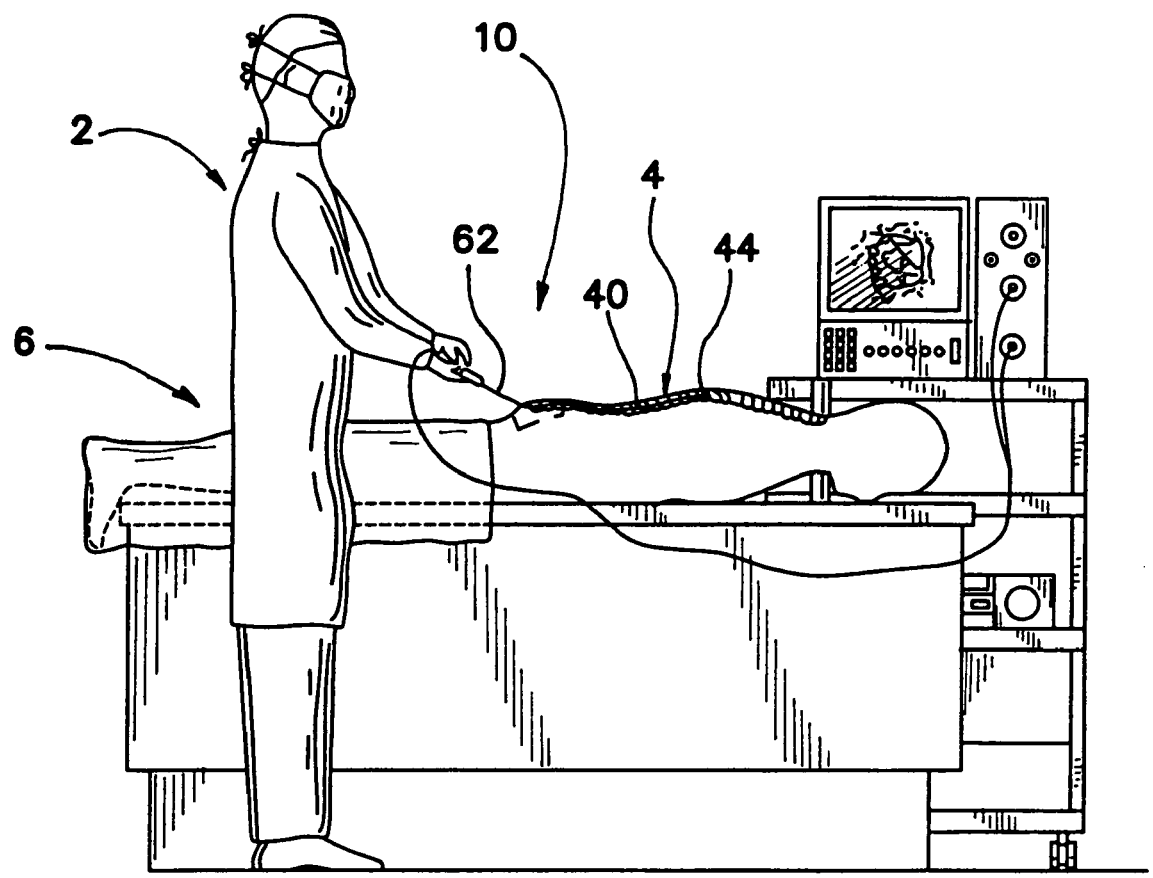
FIG. 1 is an elevational plan view of a surgical operation on a patient having an apparatus in accordance with the present invention, the apparatus being positioned through an opening in the sacrum region and into the epidural space by a physician for therapeutic treatment in accordance with a method of the present invention.

Turning now to FIG. 1, a physician 2 is shown treating and/or imaging a spine 4 of a human patient 6, using a method and apparatus 10 of the present invention.

Figure 2:
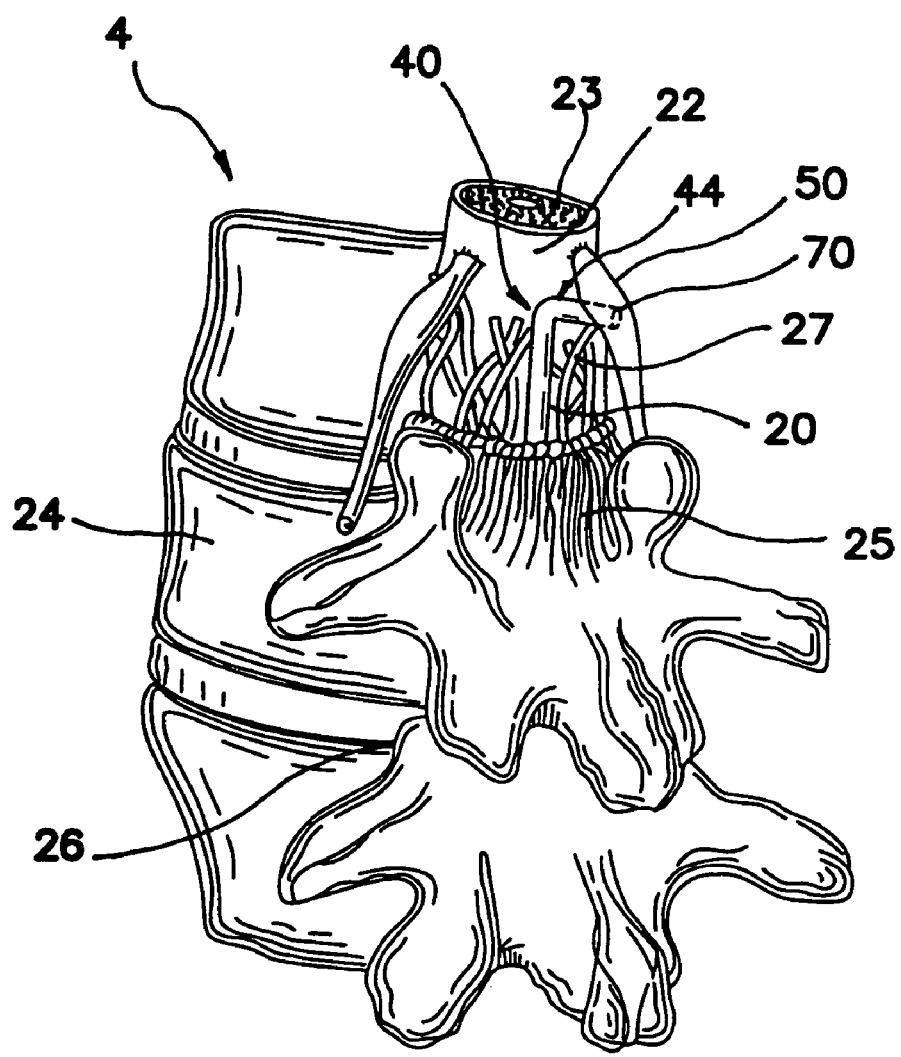
FIG. 2 is a fragmentary view of a portion of a spinal column, illustrating the positioning of a pre-formed distal region of an apparatus in accordance with the present invention, for targeting a specific nerve root.

Referring now as well to FIG. 2, in the back region or posterior end of the human body, the epidural space 20 is a potential space that is located in and extends the length of the spine 4. The epidural space 20 has a generally cylindrical or crescent type shape and is defined along one edge or side by the dura mater 22, which surrounds the spinal cord 23. The epidural space 20 is further defined along a second edge or side by the periosteum of the bony vertebrae 24 or by the ligamentum-flavum 25 at the vertebral interspaces 26. Along the interior surface of the ligamentum-flavum 25 lies the venus plexus 27, a complex configuration of veins. The epidural space 20 is a collapsible potential space that contains fat, connective tissue, blood vessels, lymphatic vessels, nerve fibers, and other structures. Various lesions, cystical masses, and nerve damage can occur in and around the epidural space, which causes various back problems for the human body. For example, fibrosis ranging from soft to tougher scar tissue may form randomly or in layers and adhere to the dura mater 22 and the periosteum of the body vertebrae 20 or the ligamentum-flavum 25, which form lesions extending across the epidural space 20. These lesions can be caused by post operative scarring of nerves such as from laminectomy procedures. A ruptured, leaking, or torn disk can also cause lesions which are often the source of back pain.

The apparatus 10 in accordance with the present invention generally comprises a catheter device 40, which is constructed, for example, from a plastic extrusion having a size of about 3 to about 25 French outer diameter. The catheter device 40 includes a distal region 44 having a pre-formed configuration, preferably defining at least one bend, angle, curve or other deformed configuration, selected to facilitate access to a specific structure of the spinal column, for example, but not limited to, a specific, targeted nerve root 50.

It is noted that the term "curve" as used herein, is not to be considered as being limited to a rounded, arcuate contour, but is intended to include any configuration that includes one or more arcs, angles, bends, non-linear configurations, or other configurations that generally do not lie along a longitudinal axis of the balance of the catheter device.

Although, for the sake of simplicity, the present description primarily will be limited to discussion of a targeted nerve root, it should be appreciated that with appropriate modification to the present apparatus, for example, with appropriate modification to the pre-formed configuration of the distal region 44 of the catheter device 40, the apparatus 10 can be used for accessing other healthy or diseased body tissues, foreign matter, or any other structure in proximity to the epidural space, such modification or modifications being considered to be within the scope of the present invention.

The catheter device 40 preferably has a durometer or hardness and construction such that the catheter device 40 can be relatively easily straightened for insertion and advancement along the epidural space and not cause significant injury to the patient. In addition, the catheter device 40 preferably is sufficiently rigid or has a sufficient stiffness for retaining the pre-formed configuration of the distal region 44 especially at body temperature.

For example, the catheter device 40 may be made of a suitable polymer or copolymer, such as polyethylene, polyurethane, nylon and the like and combinations thereof. Manufacturing techniques such as extruding, molding, wire braiding and the like may be employed.

The catheter device 40 is structured, for example, sized, to be placed in the epidural space 20 of the spine 4, or spinal canal, of a patient 6. Preferably, the pre-formed distal region 44 includes a primary curve reflected away from the longitudinal axis of the catheter device, for example, a primary curve reflected downward, in a retrograde direction, at least about 90 degrees, and preferably up to about 160 degrees, measured from a longitudinal axis of the longitudinal axis of the catheter device. For example, FIG. 2 shows a distal region 44 of the catheter device 40 having a primary curve of about 90 degrees.

It is to be appreciated that the primary curve may be selected to facilitate access to a specific targeted nerve root within the spinal canal of the patient, and therefore will preferably have a pre-formed configuration that will provide the best access the targeted nerve root based on imaging samples from the patient and/or from knowledge of the location and position of the various nerve roots in the normal human or animal spine.

Referring now to FIG. 3, preferably, the catheter device 40 further includes a lumen 58 extending from a proximal region 62 (see FIG. 1) of the catheter device 40 to the distal region 44, the lumen 58 preferably being sized to accommodate a guidewire 66 for straightening the pre-formed curve of the distal region 44. (The distal region 44 of the catheter device 40 is shown, by means of phantom lines, in a straightened configuration due to guidewire 66 located therein).

Advantageously, the catheter device 40 is structured to be straightened by being advanced along a guidewire within the epidural space in an anterograde direction. The catheter device 40 is further structured to assume or resume its pre-formed configuration, sweeping across the epidural space such that the distal tip 70 of the catheter device is located in proximity to the targeted nerve root 50, when the guidewire 66 is withdrawn or otherwise removed from the lumen 58.

Preferably, the distal region 44 of the catheter device 40 has a length or diameter about equal to or greater than the posterior vertebral canal space, allowing the distal tip 70 to engage a pedicle above the targeted nerve root and to be supported by the opposite wall of the spinal canal, for example against the wall defined by the dura matter.

Structure, for example, the catheter device lumen 58, may be provided for delivering to the nerve root 50, an agent, for example, an active agent such as a medicament 76 and/or an imaging fluid, for example, a radio-opaque dye.

Alternatively or additionally, the apparatus 10 may be configured to provide a form of energy through the distal region 44 or distal tip 70 to the nerve root 50, by means of an energy source 82, for example, for causing tissue ablation, electrical stimulation in or in proximity to the targeted nerve root 58.

More specifically, the catheter device 40 may be structured and adapted for easy injection of radio-opaque liquid contrast, local anesthetic, corticosteroid, and other indicated materials, for example, solutions and the like. Diagnostic epidurograms and neurograms can be obtained using the catheter device 40 to direct specific therapies. A radio-opaque tip may be used to verify location of the tip of the catheter. The catheter device 40 may have a smooth or slippery surface on the inner circumference and a large internal diameter to allow devices to be passed through it to treat the nerve root as desired.

FIGS. 4a and 4b show additional pre-formed configurations of distal regions 44a, 44b, and 44c of apparatus in accordance with the present invention.

For example, referring to FIG. 4a, the distal region 44a of the catheter device may include region 44ai which defines a primary curve of about 120 degrees, and a region 44aii which defines a more distally located secondary curve. This variation of the catheter device is designed for use in accessing nerve roots within the cervical region of the spine where greater precision is desired or required.

For example, the secondary curve extends at approximately a 90 degree angle as shown, in order to allow the catheter device 40a to selectively access the ventral area of the spinal canal at or near the site of insertion of the recurrent meningeal nerves onto the posterior lateral disc margin. Heretofore, this area of the spinal canal has been relatively inaccessible using conventional spinal catheters.

FIG. 4b illustrates a pre-formed distal region 44b including a region that is essentially straight, but is disposed at an angle (in this case, an angle of about 100 degrees, with respect to a longitudinal axis of the catheter device 40b.

Preferably, in all embodiments of the present invention, the pre-curved shape of the distal region 44, 44a, 44b, allows selective placement of the tip 70, 70a, 70b of the catheter device 40, 40a, 40b into the perineural tissue surrounding the segmental nerve root from a slightly retrograde approach. The degree of retrograde angulation of the catheter device is preferably level-specific, consistent with segmental variations in the angle of nerve root exit. In some embodiments of the invention, a soft distal tip is provided to reduce risk of trauma.

Turning back now to FIG. 1, methods of treating a human or animal patient, for example, methods of accessing or treating a spine of a human or animal patient, are also provided by the present invention. For example, a method of accessing and/or treating a spine or an area in proximity to a spine, in accordance with the present invention, generally comprises providing a catheter device, preferably one of the catheter devices described elsewhere herein, providing a distal region of the catheter device in a substantially straightened configuration, introducing the distal region into a sacral hiatus of a human or animal patient and advancing, while in the straightened configuration, the distal region of the catheter device anterogradely through the epidural canal from the sacral hiatus to a site adjacent a targeted nerve root. The step of advancing may include advancing the distal region to at least about the $L_4$ vertebra and up to at least about the $T_{12}$ vertebra.

Importantly, the method of the present invention further comprises positioning a distal tip of the catheter device in proximity to, for example, in contact with, the targeted nerve root by causing the distal region to substantially resume the performed configuration while the distal region is substantially or entirely located within the epidural space.

For example, in accordance with a method of the present invention, the straightened distal region of the apparatus is initially placed in standard anterograde fashion into the epidural space within the sacral area of the spinal canal. A needle may be used to access the sacral foramen. For example, the ligamentum-flavum is pierced and the needle tip is inserted into the sacral hiatus. Under fluoroscopic guidance, a guidewire, for example a straight tip floppy guidewire, is inserted and advanced through the needle and into the epidural space. The guidewire is preferably radio-opaque and formed of stainless steel with a Teflon coating. The physician then preferably fluoroscopically observes the position of the guidewire in the epidural space and advances the guidewire to a site, and preferably slightly cephalic to, the targeted nerve root. The catheter device preferably has a structure and length enabling the distal tip of the device to be advanced from the sacral hiatus to at least about the $L_4$ vertebrae, and up to and not limited to about the $T_{12}$ vertebrae. The needle may be extracted from the epidural space and discarded.

A pre-formed catheter device, preferably a catheter device in accordance with the present invention including the pre-formed distal region is then inserted over the guidewire and into the opening to the epidural space.

The guidewire functions in part as a guidance device as the catheter is advanced into the sacral hiatus. Additionally, the guidewire functions to cause the pre-formed configuration of the distal region of the catheter device to become straightened as the catheter device is passed over the guidewire.

The method in this embodiment of the invention includes the step of withdrawing the guidewire to cause the distal region to resume its preformed configuration while in the epidural space. For example, once in the appropriate position, the guidewire is at least partially withdrawn from the catheter lumen, which causes the distal region of the catheter device to substantially assume or resume its pre-formed configuration, thereby allowing the distal region to move in a somewhat retrograde direction, sweeping across the epidural space, and contacting or otherwise providing access to the targeted nerve root. The step of positioning preferably includes buttressing the catheter device against a wall of the epidural space and preferably further includes engaging a pedicle located adjacent, for example, above, the nerve root of interest.

At this point, the catheter device may be manipulated by torque if desired, and advanced or retracted until it engages the nerve root of interest. Contrast neurogram injections may be used to verify location of the catheter and to give an adequate image of the nerve root.

The methods of the present invention may further comprise performing a medical procedure on the targeted nerve root, including accessing the targeted nerve root with the distal tip of the catheter device.

The catheter device in accordance with the present invention may include more than one lumen. Devices for example may be placed through the catheter device, in accordance with the present invention, into the nerve root area. Examples of such devices include electrical stimulating devices, drug infusion catheters, epiduroscopes, neuroablation devices, cutting tools, laser fibers, and the like.

The catheter device may be structured to treat the nerve root area. For example, an electrical stimulating catheter device may include electrodes placed at the distal tip of the pre-shaped distal region. The advantage of this design is in allowing the nerve pain signal-blocking characteristic of the stimulating catheter to be directed very close to the nerve fibers of the targeted nerve root, where the signal is emanating in order to reduce the power requirements of the signal generator and therefore the size requirements of the generator. Alternatively, a drug infusion catheter device may be provided, the catheter device being structured to deliver pain management drugs directly to the pain generating fibers of the nerve root therefore reducing the concentrations and volume of the drugs needed to block the pain signals. Additionally, a neuroablative catheter device with temperature measurement capabilities could be provided which is structured to deliver neuroablative energy such as RF energy or cryogenic temperatures to the nerve root area.

The step of advancing the distal region of the catheter device preferably comprises advancing the distal region from the sacral hiatus to at least as far as a $L_4$ vertebra, and in some embodiments, at least as far as a $T_{12}$ vertebra.

The following non-limiting examples illustrate certain aspects of the present invention.

EXAMPLE 1

A 30-yr-old man is disabled from work because of 10 months of persistent thoracic pain resulting from a fall. His pain is located in the mid back area just below the scapula, radiating midline about three to four inches on either side of the spine. It does not radiate into the anterior chest, arms, or legs. It is worsened by any activity. The patient complains that he is unable to sit or stand for extended periods of time and had not slept well since his injury. At the time of the patient's presentation for treatment he states that in the past he had taken carisoprodol up to four times a day, but has since discontinued the oral narcotics because they brought no relief. He had also been going to an urgent care center about one to three times per week to receive intramuscular meperidine hydrochloride. This treatment allowed him to rest for one night after the intramuscular injection. He describes his pain as a tearing sensation in his back and he has been unable to work since his accident.

Neurological examination shows the upper and lower extremities of the cranial region are within normal limits. However, X-rays show a compression fracture at T5.

The patient states that he has been told in the past that he is not a surgical candidate, primarily due to the nature and location of the pain.

The patient is told that he is a good candidate for a therapeutic treatment using an epidural nerve root access catheter in accordance with the present invention for the injection of a steroid into the right nerve root at the T5 level. The patient consents to treatment methods in accordance with the present invention.

The patient's thoracic spine is imaged to determine an angle of the nerve roots at the T5 level. It is determined that the nerve root of interest is positioned at an angle of about 100 degrees.

A sterile catheter device, in accordance with the present invention, having a lumen along a length thereof and a pre-formed curve of about 100 degrees within a distal region thereof, is selected by the physician.

With the patient in the prone position, his sacral area is prepared and draped as a sterile field. The epidural space is entered through the sacral hiatus with a 17-gauge Tuohy needle. A 0.9 mm guidewire is inserted into and advanced along the epidural space. The distal region of the selected, pre-formed catheter device is inserted through the needle and advanced over the guidewire, assisted by fluoroscopic guidance, to the level of the T5 vertebrae. Once the distal tip of the catheter device is positioned about 3 cm cephalad of the right T5 nerve root, the guidewire is slowly retracted.

The retraction of the guidewire causes the distal tip of the catheter device to slowly sweep across the spinal canal as the distal portion resumes its pre-formed curve of about 100 degrees. The portion of the catheter immediately proximal to the curved distal portion becomes buttressed against a wall of the epidural space opposing the T5 nerve root.

Using fluoroscopic guidance, the physician gently rotates the exterior proximal portion of the catheter device until the somewhat retrograde distal region of the catheter device is pivoted into engagement with a pedicle above the T5 nerve root and the tip of the catheter device is disposed substantially in contact with the targeted nerve root. A selected steroid medication is then delivered through the lumen and into the nerve root.

After delivery of the steroid medication, the guidewire is reintroduced into the distal region of the catheter lumen, causing the preformed curve to straighten. The catheter device and guidewire are, together, carefully retracted from the epidural space.

The patient complains of postprocedural discomfort at the catheter insertion site, and describes the pain as being moderate pain made worse with activity. This pain diminishes over the next 3 days and is treated effectively with 6–8 percocets per day. However, there is an immediate decrease in the thoracic pain of which the patient originally complained. The patient is slowly tapered off oral pain medication and rehabilitation is continued until the patient is essentially pain free. The thoracic fracture heals and the patient remains pain-free.

EXAMPLE 2

In a similar example, a fiberoptic scope is introduced into the straightened catheter lumen disposed at a site of interest in a spine of a patient, until the tip of the fiberoptic scope is positioned at about the distal tip of the catheter device. A video camera is connected to a proximal portion of the fiberoptic scope in order to view the targeted nerve root prior to the intended treatment. Gentle irrigation with normal saline is used to distend the epidural space, especially at the area of the epidural space near the catheter tip. The catheter and fiberoptic are advanced cephalad, caudad, and rotated clockwise and counterclockwise to obtain an accurate image of the $T_{10}$ space. The right $T_{-10}$ root is viewed on a video screen and it is noted that the nerve root appears to be encased with both a fibrous and a cottony material. The cottony material is moved aside with a gentle stream of normal saline. Behind it, an area of erythema is observed lateral to the right $T_{-10}$ root. Triamcinalone 80 mg in 10 mL of normal saline is injected onto the nerve root and contiguous structures. The catheter device is carefully removed as noted in EXAMPLE 1.

While this invention has been described with respect to various specific examples and embodiments, it is to be understood that the invention is not limited thereto and that it can be variously practiced within the scope of the following claims.

What is claimed is:

1. A method of treating a human or animal patient, the method comprising the steps of:
   providing a catheter device, sized to be placed in an epidural space of a spinal canal of a human or animal patient, the catheter device having a distal region with a pre-formed configuration including at least one curve and a distal tip;
   providing the distal region of the catheter device in a substantially straightened configuration;
   introducing the distal region of the catheter device into a sacral hiatus of a human or animal patient;
   advancing, while in a straightened configuration, the distal region of the catheter device anterogradely through the epidural canal from the sacral hiatus to a site adjacent a targeted nerve root; and
   positioning the distal tip of the catheter device in proximity to the targeted nerve root by causing the distal region of the catheter device to resume the pre-formed configuration.

2. The method according to claim 1 wherein the step of providing the distal region of the catheter device in a substantially straightened configuration includes providing a guidewire within a lumen of the catheter device.

3. The method according to claim 1 wherein the preformed configuration includes a primary curve of at least about 90 degrees.

4. The method according to claim 1 wherein the preformed configuration of the distal region of the catheter device includes a primary curve and a secondary curve.

5. The method according to claim 1 further comprising a step of performing a medical procedure on the targeted nerve root including accessing the targeted nerve root with the distal tip of the catheter device.

6. The method according to claim 1 wherein the step of positioning includes buttressing the catheter device against a wall of the spinal canal generally opposing the target nerve root.

7. The method of claim 1 wherein the step of advancing comprises advancing the distal region from the sacral hiatus to at least as far as a L4 vertebra.

8. A method of treating a human or animal patient, comprising:
   providing a catheter device, sized to be placed in an epidural space of a spinal canal of a human or animal patient, the catheter device having a distal region with a pre-formed configuration including at least one curve, a distal tip, and a lumen extending from a proximal region of the catheter device to the distal region, the lumen being sized to accommodate a guidewire;
   introducing the catheter device into the spinal canal of the patient, the catheter device being introduced while in a relatively straight configuration obtained by having a guidewire located within the lumen;
   advancing the catheter device anterogradely along an epidural space of the spinal canal of the patient to a site such that the distal region of the catheter device is disposed adjacent a targeted nerve root; and
   positioning the distal tip of the catheter device in proximity to the targeted nerve root by withdrawing the guidewire from the catheter device lumen so that the distal region of the catheter device assumes its pre-formed configuration.

9. The method according to claim 8 wherein the preformed configuration includes a primary curve of at least about 90 degrees.

10. The method according to claim 8 wherein the preformed configuration of the distal region of the catheter device includes a primary curve and a secondary curve.

11. The method according to claim 8 further comprising a step of introducing an active agent from the distal tip of the catheter device into the targeted nerve root.

12. The method according to claim 8 wherein the step of positioning includes buttressing the catheter device against a wall of the spinal canal generally opposing the targeted nerve root.

13. The method of claim 8 wherein the step of advancing comprises advancing the distal region from the sacral hiatus to at least as far as a L4 vertebra.

* * * * *